United States Patent
Soffer et al.

(10) Patent No.: US 8,538,534 B2
(45) Date of Patent: *Sep. 17, 2013

(54) SYSTEMS AND METHODS FOR ELECTRICALLY STIMULATING THE LOWER ESOPHAGEAL SPHINCTER TO TREAT GASTROESOPHAGEAL REFLUX DISEASE

(75) Inventors: Edy E. Soffer, Los Angeles, CA (US); Jeffrey Conklin, Los Angeles, CA (US)

(73) Assignee: Endostim, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/419,255

(22) Filed: Mar. 13, 2012

(65) Prior Publication Data

US 2012/0232610 A1      Sep. 13, 2012

Related U.S. Application Data

(63) Continuation of application No. 12/300,614, filed as application No. PCT/US2007/068907 on May 14, 2007, now Pat. No. 8,160,709.

(51) Int. Cl.
*A61N 1/36* (2006.01)

(52) U.S. Cl.
USPC .......................................................... 607/40

(58) Field of Classification Search
USPC ................. 607/2, 40, 41, 115, 116, 124, 133
See application file for complete search history.

(56) References Cited

U.S. PATENT DOCUMENTS

| | | | |
|---|---|---|---|
| 4,612,934 A | 9/1986 | Borkan | |
| 5,117,827 A | 6/1992 | Stuebe et al. | |
| 5,231,988 A | 8/1993 | Wernicke et al. | |
| 5,292,344 A | 3/1994 | Douglas | |
| 5,423,872 A | 6/1995 | Cigaina | |
| 5,690,691 A | 11/1997 | Chen et al. | |
| 5,716,385 A | 2/1998 | Mittal et al. | |
| 5,836,994 A | 11/1998 | Bourgeois | |
| 5,861,044 A | 1/1999 | Crenshaw | |
| 6,041,258 A | 3/2000 | Cigaina et al. | |
| 6,097,984 A | 8/2000 | Douglas | |
| 6,216,039 B1 | 4/2001 | Bourgeois | |
| 6,285,897 B1 | 9/2001 | Kilcoyne et al. | |
| 6,321,124 B1 | 11/2001 | Cigaina | |
| 6,381,495 B1 | 4/2002 | Jenkins | |
| 6,449,511 B1 | 9/2002 | Mintchev et al. | |

(Continued)

FOREIGN PATENT DOCUMENTS

| | | |
|---|---|---|
| WO | PCT/US98/10402 | 12/1998 |
| WO | PCT/US00/09910 | 10/2000 |

(Continued)

OTHER PUBLICATIONS

Ellis, et al., "The Prevention of Experimentally Induced Reflux by Electrical Stimulation of the Distal Esophagus", American Journal of Surgery, vol. 115, Apr. 1968, 482-487.

(Continued)

*Primary Examiner* — Brian T Gedeon

(57) ABSTRACT

The present specification describes methods and devices using electrical stimulation to modulate lower esophageal sphincter (LES) pressure. The electrical stimulation may be delivered to the LES via one or more electrodes that is placed in contact with the LES tissue. The methods and devices are useful to treat a number of conditions or disease conditions, including for example, gastroesophageal reflux disease (GERD).

20 Claims, 8 Drawing Sheets

(56) References Cited

U.S. PATENT DOCUMENTS

| | | |
|---|---|---|
| 6,510,332 B1 | 1/2003 | Greenstein |
| 6,587,719 B1 | 7/2003 | Barrett et al. |
| 6,591,137 B1 | 7/2003 | Fischell et al. |
| 6,611,715 B1 | 8/2003 | Boveja |
| 6,615,084 B1 | 9/2003 | Cigaina |
| 6,678,561 B2 | 1/2004 | Forsell |
| 6,754,536 B2 | 6/2004 | Swoyer et al. |
| 6,760,626 B1 | 7/2004 | Boveja |
| 6,826,428 B1 | 11/2004 | Chen et al. |
| 6,832,114 B1 | 12/2004 | Whitehurst et al. |
| 6,879,859 B1 | 4/2005 | Boveja |
| 6,901,295 B2 | 5/2005 | Sharma |
| 7,006,871 B1 | 2/2006 | Darvish et al. |
| 7,076,306 B2 | 7/2006 | Marchal et al. |
| 7,114,502 B2 | 10/2006 | Schulman et al. |
| 7,146,216 B2 | 12/2006 | Bumm |
| 7,310,557 B2 | 12/2007 | Maschino et al. |
| 2003/0144708 A1 | 7/2003 | Starkebaum |
| 2004/0012088 A1 | 1/2004 | Fukasawa et al. |
| 2004/0015201 A1 | 1/2004 | Greenstein |
| 2004/0024428 A1 | 2/2004 | Barrett |
| 2004/0039427 A1 | 2/2004 | Barrett |
| 2004/0193229 A1 | 9/2004 | Starkebaum et al. |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2006/0036293 A1 | 2/2006 | Whitehurst et al. |
| 2006/0064037 A1 | 3/2006 | Shalon et al. |
| 2006/0116736 A1 | 6/2006 | DiLorenzo |
| 2006/0167498 A1 | 7/2006 | DiLorenzo |
| 2006/0206160 A1 | 9/2006 | Cigaina et al. |
| 2007/0106337 A1 | 5/2007 | Errico et al. |
| 2007/0162085 A1 | 7/2007 | DiLorenzo |
| 2008/0021512 A1 | 1/2008 | Knudson et al. |
| 2008/0154191 A1 | 6/2008 | Gobel |

FOREIGN PATENT DOCUMENTS

| | | |
|---|---|---|
| WO | PCT/US00/10154 | 10/2000 |
| WO | WO/00/61223 | 10/2000 |
| WO | WO/00/61224 | 10/2000 |
| WO | WO02/43467 | 6/2002 |
| WO | WO2005/051486 | 9/2005 |

OTHER PUBLICATIONS

"Impact of Fundoplication on Bolus Transit Across Esophagogastric Junction", Kahrilas et al., American Physiological Society, 1998, 1386-1393.

"Electrical Stimulation of Esophageal Smooth Muscle and Effects of Antagonists", Lund et al., American Journal of Physiology, vol. 217, No. 5, Nov. 1969, 1369-1374.

"Three-dimensional Imaging of the Lower Esophageal Sphincter in Gastroesophageal Reflux Disease," Stein et al., Annual Meeting of the American Surgical Association, Apr. 11-13, 1991, 374-383.

"Different Responsiveness of Excitatory and Inhibitory Enteric Motor Neurons in the Human Esophagus to Electrical Field Stimulation and to Nicotine", Gonzalez et al., Am J Physiol Gastrointest Liver Physiol, 287:G299-G306, 2004.

"Neurocardiac and Cerebral Responses Evoked by Esophageal Vago-Afferent Stimulation in Humans: Effects of Varying Intensities", Kamath et al., Cardiovascular Research, 40 (1998) 591-599.

"Physiologic Specialization at Esophagogastric Junction in Three Species", Christensen et al., American Journal of Physiology, vol. 225, No. 6, Dec. 1973, 1265-1270.

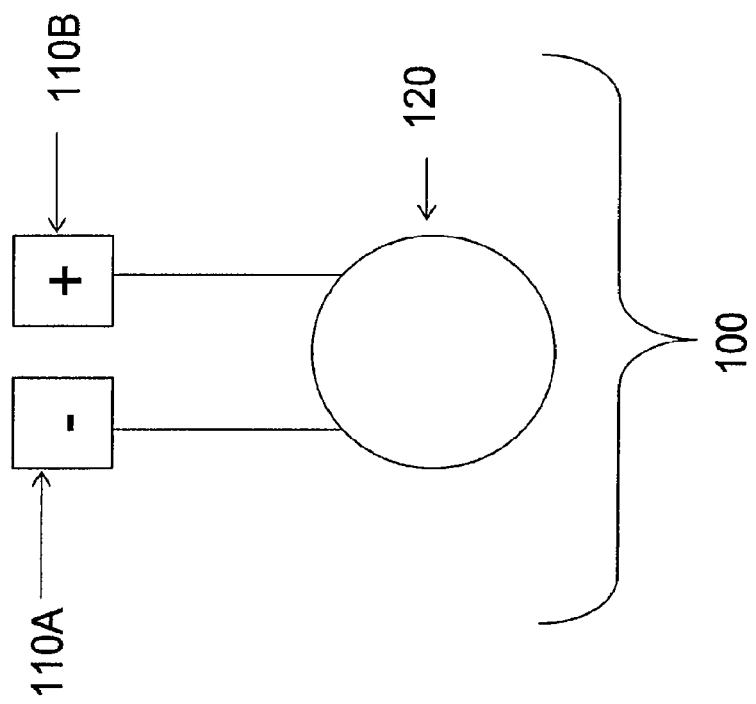

SYSTEMS AND METHODS FOR ELECTRICALLY STIMULATING THE LOWER ESOPHAGEAL SPHINCTER TO TREAT GASTROESOPHAGEAL REFLUX DISEASE

CROSS REFERENCE

The present specification is a continuation of U.S. patent application Ser. No. 12/300,614, now U.S. Pat. No. 8,160,709, filed on Nov. 12, 2008, which calls priority to PCT Application No. PCT/US07/68907, filed on May 14, 2007.

FIELD

This invention relates to the use of electrical stimulation to modulate lower esophageal sphincter pressure.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Electrical stimulation of the stomach has been shown to modulate lower esophageal sphincter pressure. Electrical stimulation using neural gastrointestinal electrical stimulation ("NGES") at high frequency can induce contractions of the smooth muscle of the gut.

The LES is a band of muscles at the junction of the stomach and the esophagus; when closed, the LES prevents the reflux of stomach contents into the esophagus. Gastroesophageal reflux disease ("GERD") occurs when the LES does not close properly and stomach contents reflux into the esophagus. Increasing LES pressure may be useful in treating GERD.

Approximately 20% of the U.S. population experience weekly reflux symptoms. GERD is characterized by symptoms and/or tissue damage due to prolonged exposure of the esophagus to the acidic contents of the stomach. Two of the most common symptoms of GERD include chronic heartburn and regurgitation of acid. Chronic heartburn places a person at a greater risk for complications such as strictures, Barrett's esophagus (a pre-cancerous disease), and esophageal cancer. Approximately 10% of patients who have GERD develop Barrett's esophagus and of those patients, approximately 1% will develop esophageal cancer.

Treatment for GERD is maintained on a long-term basis, even after symptoms are brought under control. Current treatment methods include lifestyle changes, use of medications and surgical procedures. Lifestyle changes include avoiding factors that may aggravate the symptoms of GERD. Current medications available are promotility drugs to improve the movement of food from the stomach and increase LES pressure, H2 blockers to reduce acid production by the stomach and proton pump inhibitors to limit acid secretion in the stomach. H2 blockers and proton pump inhibitors allow resolution of symptoms and healing of the esophagus. Surgical treatment includes the Nissen's Fundoplication, which involves wrapping the stomach around the esophagus. Endoscopic treatments, when appropriate, are also available. In one endoscopic procedure, radiofrequency energy is delivered to the gastroesophageal junction to form scar tissue to strengthen the LES (i.e., the Stretta™ procedure). In another endoscopic procedure, sutures are use to alter the pathway between the stomach and esophagus (i.e., the EndoCinch™ procedure).

However, these treatment options carry disadvantages and shortcomings. Recently, two promotility agents, cisapride and tegaserod, were removed from the market due to potentially serious complications that had been reported. Nissen's Fundoplication is an invasive surgery and the new endoscopic treatments lack long-term data on their safety and success. Most drug therapies do not modulate LES pressure, which is an underlying cause of GERD. Thus, there exists a need for alternative treatment options for modulating LES pressure as well as for treatment of conditions caused by or related to abnormal LES pressure, including, for example, GERD.

SUMMARY

The following embodiments and aspects thereof are described and illustrated in conjunction with compositions and methods which are meant to be exemplary and illustrative, not limiting in scope.

The present specification describes a method of modulating lower esophageal sphincter (LES) pressure in a subject in need thereof, comprising providing an electrical signal; and delivering the electrical signal to a LES or a proximate region to the LES to stimulate the LES. In one embodiment, delivering the electrical signal may comprise using a stimulation device configured to generate and deliver the electrical signal to the LES or the proximate region to the LES. The stimulation device may comprise one or more electrodes adapted for placement in contact with the LES or the proximate region to the LES tissue; and an electrical signal generator. In one embodiment, at least a portion of the one or more electrodes may be positioned on the LES. In another embodiment, at least a portion of the one or more electrodes may be positioned on the proximate region to the LES. In another embodiment, the one or more electrode(s) may be positioned along a longitudinal axis of the LES.

In one embodiment, the electrical signal of the method may comprise low frequency electrical pulses to increase the LES pressure. In one embodiment, the frequency of the low frequency electrical pulses may be a frequency of less than 60 pulses per minute. In another embodiment, the frequency of the low frequency electrical pulses may be about 6 pulses per minute. Further, the electrical signal of the method may have a pulse duration of about 10 milliseconds to about 500 milliseconds and a pulse amplitude of about 5 mAmp to about 10 mAmp.

In another embodiment, the electrical signal of the method may comprise high frequency electrical pulses to decrease the LES pressure. In another embodiment, the electrical signal may have a train duration of about 2 milliseconds to about 300 microseconds. In a particular embodiment, the frequency of the high frequency electrical pulses may be a frequency of about 50 Hz and the electrical signal may further comprise a train duration of about 6 seconds, a pulse duration of about 20 milliseconds, a pulse amplitude of about 10 volts and a pulse interval of about 60 seconds.

The present specification also describes a method of treating a condition or disease condition related to or caused by abnormal lower esophageal sphincter (LES) pressure in a subject in need thereof, comprising providing an electrical signal; and delivering the electrical signal to the LES or a proximate region to the LES to stimulate the LES. Delivering the electrical signal may comprise using stimulation device configured to generate and deliver the electrical signal to the LES or the proximate region to the LES. The implantable stimulation device may comprise one or more electrodes adapted for placement on the LES; and an electrical signal generator. In one embodiment, at least a portion of the one or more electrodes may be placed in contact with the LES. In another embodiment, at least a portion of the one or more electrodes may be placed in contact with a proximate region to the LES. In another embodiment, the one or more electrode(s) may be positioned along a longitudinal axis of the LES.

In one embodiment, the electrical signal of the method may comprise low frequency electrical pulses to increase the LES pressure to treat the condition or disease condition. The frequency of the low frequency electrical pulses may a frequency of less than 60 pulses per minute. In a particular embodiment, the frequency of the low frequency electrical pulses may be about 6 pulses per minute. In a further embodiment, the electrical signal may have a pulse duration of about 10 milliseconds to about 500 milliseconds and a pulse amplitude of about 5 mAmp to about 10 mAmp.

In another embodiment, the electrical signal of the method may comprise high frequency electrical pulses to decrease the LES pressure to treat the condition or disease condition. In another embodiment, the electrical signal may have a train duration of about 2 milliseconds to about 300 microseconds. The frequency of the high frequency electrical pulses may be about 50 Hz and the electrical signal may further comprise a train duration of about 6 seconds, a pulse duration of about 20 milliseconds, a pulse amplitude of about 10 volts and a pulse interval of about 60 seconds.

In various embodiments the condition or disease condition may be gastroesophageal reflux disease (GERD), food reflux, acid reflux, reflux esophagitis, chronic heart burn, gastroparesis, scleroderma, hypotensive lower esophageal sphincter, extraesophageal manifestations caused by reflux (e.g., laryngoesophageal reflux, chronic couch and reflux related asthma), esophageal spasm, achalasia, or nutcracker esophagus.

Further, the present invention describes a method of decreasing esophageal pressure or treating esophageal spasm or nutcracker esophagus, comprising providing an electrical signal comprising high frequency electrical pulses; and delivering the electrical signal to a region of the esophagus above the LES to stimulate the esophageal muscle. Delivering the electrical signal may comprise using a stimulation device configured to generate and deliver the electrical signal to the region of the esophagus above the LES. The implantable device may comprise one or more electrodes adapted for placement on region of the esophagus above the LES; and an electrical signal generator. The electrical signal may further comprise a train duration of about 2 milliseconds to about 300 microseconds. The frequency of the high frequency electrical pulses may be about 50 Hz and the electrical signal may further comprises a train duration of about 6 seconds, a pulse duration of about 20 milliseconds, a pulse amplitude of about 10 volts and a train interval of about 60 seconds.

The present invention additionally describes an exogenous electrical signal adapted for delivery to a lower esophageal sphincter (LES) of a patient in need of treatment for the modulation of LES pressure or for a condition or disease condition related to or cause by abnormal LES pressure, comprising: low frequency electrical pulses, wherein the exogenous electrical signal is adapted to increase the LES pressure or to treat a condition or disease condition related to or caused by abnormally low LES pressure. The frequency of the electrical pulses may be less than 60 pulses per minute. In further embodiments, the electrical signal may further comprise a pulse duration of about 10 milliseconds to about 500 milliseconds and a pulse amplitude of about 5 mAmp to about 10 mAmp. In a particular embodiment, the frequency of the electrical pulses may be about 6 pulses per minute. In another particular embodiment, the signal may comprise a frequency of 6 pulses per minute, a pulse duration of about 375 milliseconds and a pulse amplitude of about 5 mAmp.

The present specification also describes an implantable device configured to apply the electrical signals described herein.

The present specification also describes a computer readable medium having computer executable instructions for applying an electrical signal to stimulate the lower esophageal sphincter (LES) to modulate LES pressure in a subject in need thereof or to treat a condition or disease condition related to or caused by abnormal LES pressure in a subject in need thereof, comprising: instructions to generate and deliver an electrical signal comprising low frequency pulses to increase the LES pressure or to treat a condition or disease condition caused by or related to abnormally low LES pressure; or instructions to generate and deliver an electrical signal comprising high frequency pulses to decrease the LES pressure or to treat a condition or disease condition caused by or related to abnormally high LES pressure.

The instructions to generate and deliver the electrical signal comprising low frequency pulses may further comprise instructions to generate and deliver a pulse duration of about 10 milliseconds to about 500 milliseconds and a pulse amplitude of about 5 mAmp to about 10 mAmp. In another embodiment, the instructions to generate and deliver the electrical signal comprising high frequency pulses may further comprise instructions to generate and deliver a train duration of about 2 millisecond to about 3000 microseconds. In another embodiment, the high frequency of the electrical signal may be a frequency of about 50 Hz and the instructions to generate and deliver the electrical signal comprising high frequency pulses may further comprise instructions to generate and deliver a train duration of about 6 seconds, a pulse duration of about 20 milliseconds, a pulse amplitude of about 10 volts and a pulse interval of about 60 seconds.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are considered illustrative rather than restrictive.

FIG. 7A depicts an electrical signal generator that may be configured to deliver an exogenous electrical signal in accordance with various embodiments.

DETAILED DESCRIPTION

Figure 1:
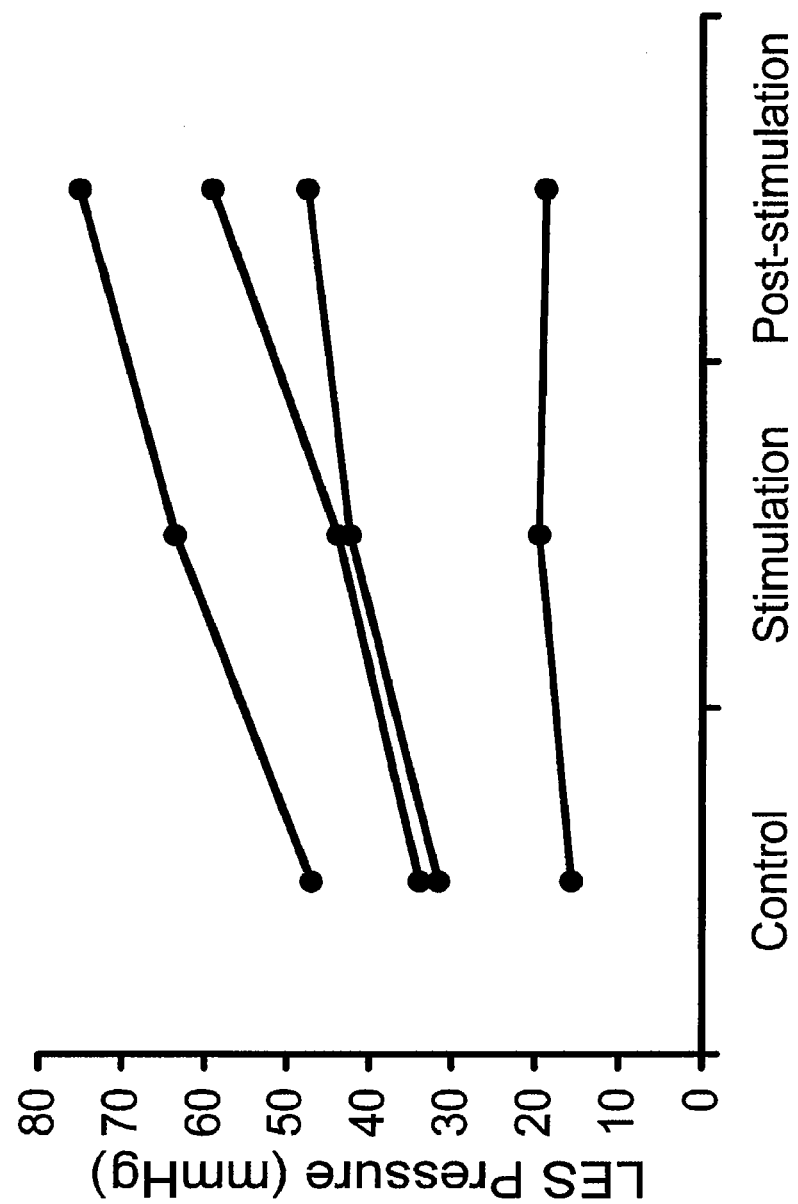
FIG. 1 depicts the effect of low frequency stimulation on lower esophageal sphincter pressure in accordance with one embodiment.
Figure 2:
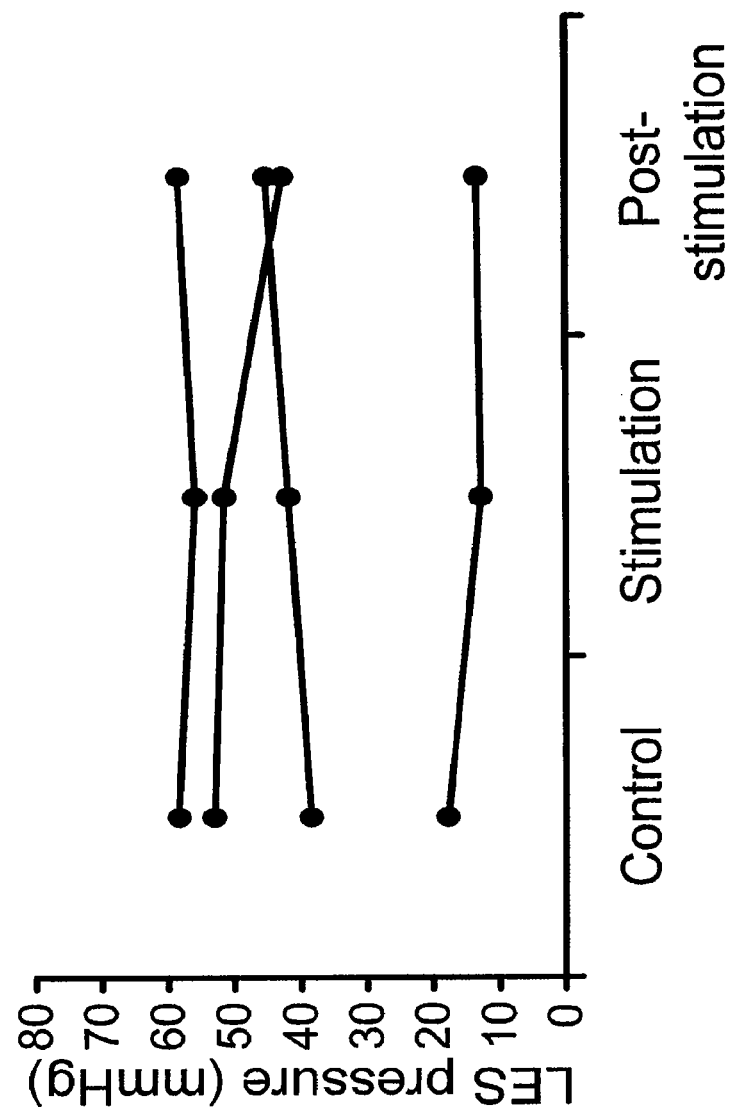
FIG. 2 depicts the effect of neural gastric electrical stimulation on lower esophageal sphincter pressure in accordance with one embodiment.
Figure 3:
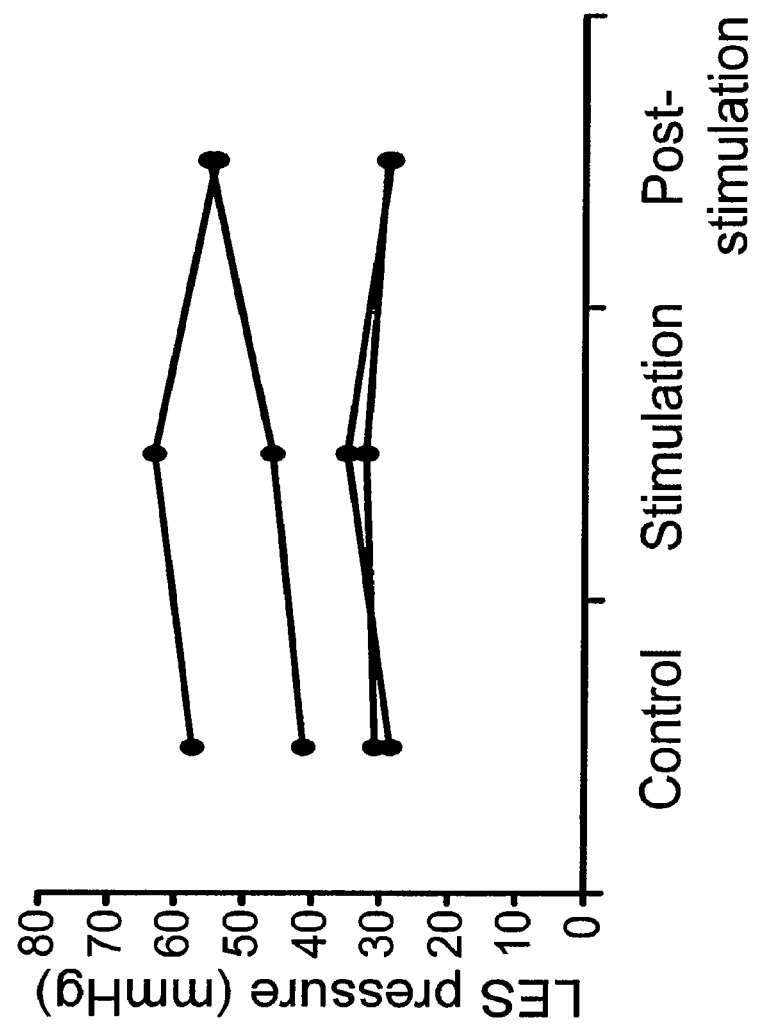
FIG. 3 depicts the effect of high frequency stimulation (50 Hz) on lower esophageal sphincter pressure in accordance with one embodiment.
Figure 4:
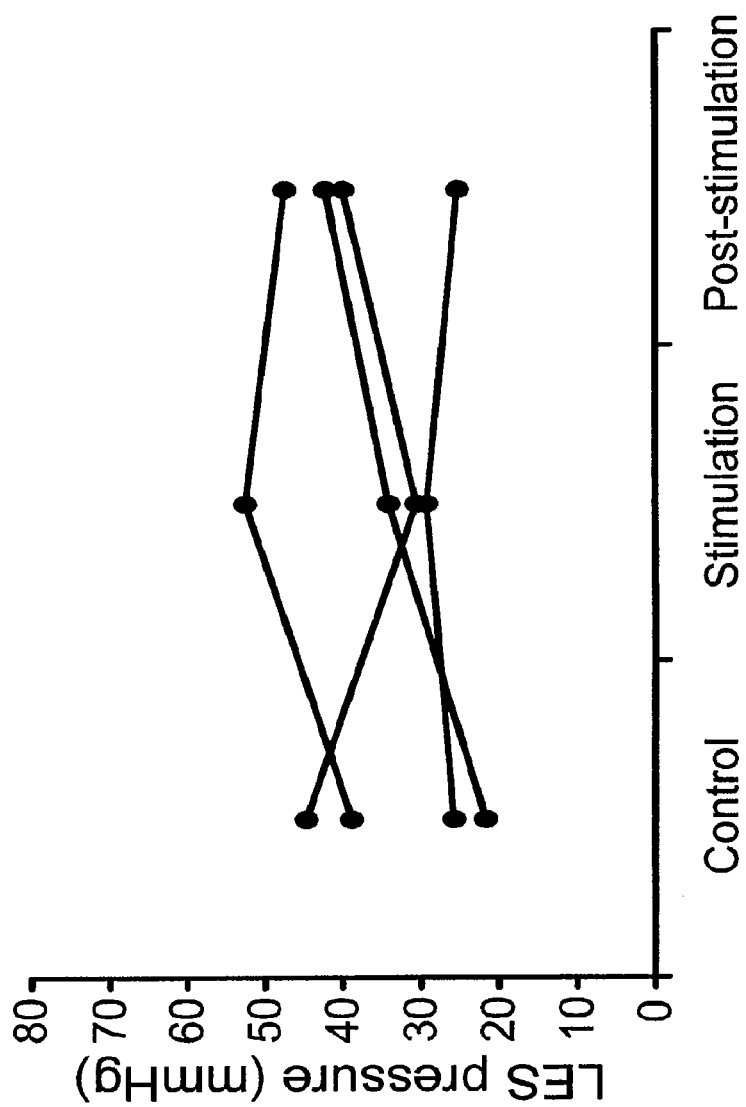
FIG. 4 depicts the effect of high frequency stimulation (20 Hz) on lower esophageal sphincter pressure in accordance with one embodiment.
Figure 5:
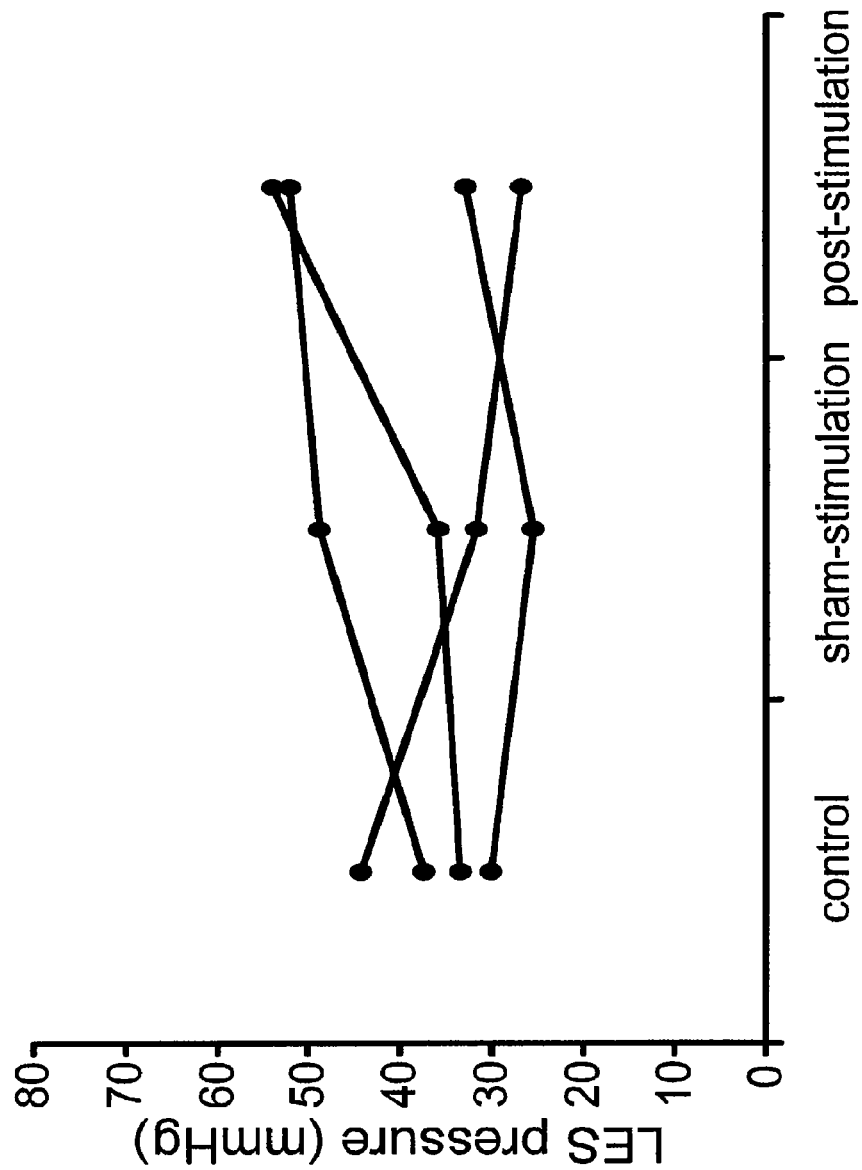
FIG. 5 depicts the effect of sham stimulation on lower esophageal sphincter pressure in accordance with one embodiment.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Mammal" as used herein refers to any member of the class Mammalia, including, without limitation, humans and non-human primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted condition or disorder even if the treatment is ultimately unsuccessful. Those in need of treatment include those already with the condition or disorder as well as those prone to have the condition or disorder or those in whom the condition or disorder is to be prevented.

"Conditions" and "disease conditions," as used herein may include, but are in no way limited to gastric reflux, gastroesophageal reflux disease ("GERD"), food or acid regurgitation, reflux esophagitis, chronic heart burn, gastroparesis, hypotensive lower esophageal sphincter, extraesophageal manifestations caused by reflux, esophageal spasm, achalasia, and nutcracker esophagus.

"Extraesophageal manifestations" as used herein with respect to reflux refers to any problem caused by reflux that is not manifested in the esophagus. Extraesophageal manifestations include, but are not limited to laryngopharyngeal and pulmonary conditions that result from a subject having a hypotensive lower esophageal sphincter. Examples of extraesophageal manifestations include but are not limited to shortness of breath, chronic cough, hoarseness of the voice, and asthma manifestations.

"Low frequency" as used herein refers to frequencies that are typically expressed in the ranges of pulse(s) per minute. For example, low frequency is generally less than 60 pulses per minute.

"High frequency" as used herein refers to frequencies that are typically expressed in the ranges of pulses per second (Hz). For example, high frequency is generally 1 Hz or greater.

The present specification describes methods and devices incorporating the use of low frequency electrical stimulation or neural high frequency stimulation to modulate lower esophageal sphincter pressure.

Direct electrical stimulation of the lower esophageal sphincter (LES) in vivo has not heretofore been studied. The inventors have found that low frequency electrical stimulation of the lower esophageal sphincter significantly increases lower esophageal sphincter pressure, and that the effect of low frequency stimulation on lower esophageal sphincter pressure is prolonged beyond the stimulation period. In subjects who have abnormally low LES pressure, the increase in LES pressure may maintain the LES in a closed state, which reduces reflux of stomach contents, including but not limited to acid. Conditions wherein increasing the LES pressure may be useful include gastroesophageal reflux disease ("GERD"), food or acid regurgitation, reflux esophagitis, chronic heart burn, hypotensive lower esophageal sphincter, and extraesophageal manifestations caused by reflux.

The inventors have further found that neural gastric electrical stimulation ("NGES") has a biphasic effect on the lower esophageal sphincter: it causes an initial contraction that is cholinergically mediated, followed by relaxation that is mediated by nitric oxide. Thus, NGES of the LES may be used to lower the LES pressure. As such, achalasia may be treated by lowering the LES pressure. Achalasia is an esophageal disorder wherein the esophagus is less able to move food towards the stomach and the LES does not relax as much as it needs to be during swallowing. Symptoms of achalasia include difficulty swallowing liquids and solids, regurgitation of food, chest pain, weight loss, heart burn and cough. Complications of achalasia may include reflux, and aspiration of food into the lungs.

Further, the inventors believe that NGES or neural high frequency stimulation of the esophageal area above the LES may be used to lower esophageal pressure or to treat conditions such as esophageal spasm and nutcracker esophagus. Esophageal spasms are uncoordinated series of muscle contractions that prevent the proper traveling of food into the stomach. Some signs and symptoms of esophageal spasms include chest pain, difficulty swallowing, painful swallowing, a sensation that an object is stuck in the throat, regurgitation, and heartburn. Nutcracker esophagus is an abnormality wherein swallowing contractions are too powerful. Symptoms of nutcracker esophagus include chest pain, dysphasia, and heartburn.

The present specification is thus directed to devices and methods to modulate lower esophageal sphincter pressure using low frequency electrical stimulation or high frequency NGES applied to the LES. The present invention is further directed to devices and methods of treating conditions or disease conditions related to or caused by abnormal lower esophageal sphincter pressure, or related to or caused by high esophageal pressure.

In one embodiment, the present specification provides a method of increasing or decreasing the LES pressure in a subject in need thereof. The method comprises providing an electrical signal and delivering the electrical signal to the LES. Delivering the electrical signal may comprise placing one or more implantable electrodes in contact with the LES tissue in a subject in need of increased LES pressure or in a subject in need of decreased LES pressure and applying electrical pulses to the LES to stimulate the LES. In one embodiment, the electrode or electrodes are positioned such that a portion of the electrode or electrodes are in contact with the LES tissue. In a particular embodiment, the electrode or electrodes or a portion thereof are placed in contact with the outer surface of the LES tissue. In a further embodiment, the increased LES pressure is prolonged for a period of time beyond the stimulation period. In one particular instance, the increased LES pressure is prolonged for at least 20 minutes. In another embodiment, the LES pressure is decreased within a few seconds of the electrical stimulation. In a particular instance, the decreased LES pressure is sustained for about 8 seconds.

In another embodiment, the present specification provides for a method of treating a condition or a disease condition related to or caused by abnormal LES pressure in a subject in need thereof. The method comprises providing an electrical signal and delivering the electrical signal to the LES. Delivering the electrical signal may comprise placing one or more implantable electrodes in contact with the LES tissue in a subject in need of treatment for a condition or disease condition related to or caused by abnormal LES pressure and applying electrical pulses to the LES to stimulate the LES. In one embodiment, the electrode or electrodes are positioned such that a portion of the electrode or electrodes are in contact with the LES tissue. In a particular embodiment, the electrode or electrodes or a portion thereof are placed in contact with the outer surface of the LES tissue.

Examples of conditions or disease conditions that may be treated by the inventive method wherein the object is to increase the LES pressure include, but are not limited to gastroesophageal reflux disease ("GERD"), food or acid regurgitation, reflux esophagitis, chronic heart burn, gastroparesis, scleroderma, hypotensive lower esophageal sphincter, extraesophageal manifestations caused by reflux, laryngopharyngeal or pulmonary conditions that result from a subject having a hypotensive lower esophageal sphincter, shortness of breath, chronic cough, hoarseness of the voice and asthma manifestations due to a hypotensive lower esophageal sphincter. Achalasia may be treated by the inventive method by decreasing the LES pressure. Further, esophageal spasm and nutcracker esophagus may be treated by the inventive method by decreasing the pressure of an area above the LES.

The electrode may be placed in contact to any level in the LES tissue, from the inner lining (i.e., mucosa) to the muscle layer. Placing the electrode in contacting with the LES tissue may be performed by any method known in the art; for example, the electrode may be surgically or endoscopically placed. One particular method comprises suturing the electrode to a muscle layer of the LES tissue. The electrode may be placed along the longitudinal axis of the LES. The LES is a band of muscles at the junction of the stomach and the esophagus. Thus, the exact boundaries of the LES may not be apparent during the placement of an electrode. As such, in accordance with an embodiment of the invention, a portion of the electrode may extend into a proximate region above or below the LES. "Proximate region" to the LES as used herein generally refers to a region up to about 3 cm above or below the LES. However, one of skill in the art will appreciate that an individual's anatomy may vary and thus, the electrode may extend into a region that is more than about 3 cm above or below the LES and is still within the scope of the invention. In one particular embodiment, the electrode may extend into a region that is up to about 2 cm above the LES. In another particular embodiment, the electrode may extend into the region that is up to about 3 cm below the LES.

For treatment of esophageal spasms or nutcracker esophagus, one or more electrodes may be placed in contact with the esophagus in a region that is above the LES and may be performed by any method known in the art.

The electrode(s) may have any dimension suitable for placement on the LES, on a proximate region to the LES, or on the esophagus in a region above the LES. In a particular embodiment, the electrode may be about 2-3 cm in length. In another particular embodiment, the electrode may be about 1-2 cm in length.

The electrical signal may comprise a variety of parameters to stimulate the LES. In one embodiment, wherein the object is to increase the LES pressure or to treat a condition or disease condition caused by or related to abnormally low LES pressure, the signal comprises low frequency pulses. In a particular embodiment, the signal comprises frequencies of about 1 pulse to about 60 pulses per minute. In another particular embodiment, the signal comprises frequencies of less than 20 pulses per minute. In another particular embodiment, the signal comprises frequencies of less than 15 pulses per minute. In another particular embodiment, the signal comprises frequencies of less than 10 pulses per minute. In another particular embodiment, the signal comprises a frequency of less than 5 pulses per minute. In another particular embodiment, the signal comprises a frequency of about 6 to about 7 pulses per minute. In another particular embodiment, the signal comprises a frequency of about 6 pulses per minute. Another parameter of the electrical signal may include a pulse duration of about 10 milliseconds to about 500 milliseconds. In a particular embodiment, the electrical signal may include a pulse duration of 375 milliseconds. Yet another parameter of the electrical signal may include a pulse amplitude of about 5 mAmp to about 10 mAmp. In a particular embodiment, the electrical signal may include a pulse amplitude of about 5 mAmp.

In another embodiment, wherein the object is to decrease the LES pressure, to treat a condition or disease condition caused by or related to having abnormally high LES pressure (e.g., achalasia), or to treat esophageal spasms or nutcracker esophagus, the signal comprises high frequency pulses. In particular embodiments, the high frequency pulses may be from about Hz to about 100 Hz. In one particular embodiment, the high frequency pulses may be about 50 Hz. In another embodiment, the signal may comprise a train duration of about 2 milliseconds to about 300 microseconds. In a particular embodiment, the train duration may be about 50 microseconds to about 300 microseconds. In another particular embodiment, the train duration may be about 2 milliseconds to about 50 microseconds.

In another particular embodiment, neural gastric electric stimulation (NGES) may be applied to the LES tissue to decrease the LES pressure, to treat a condition or disease condition caused by or related to having abnormally high LES pressure (e.g., achalasia), or to treat esophageal spasms or nutcracker esophagus. The NGES may have a frequency of about 5 Hz to about 100 Hz, a train duration of about 1 second to about 6 seconds, an amplitude of about 5 volts to about 10 volts, and a train interval of about 2 per minute to 1 every 5 minutes. "Train interval" as used with respect to NGES refers to a group of pulses, wherein each group of pulses has a duration of a given amount of time. For example, a train may last 6 seconds, given once every minute and within each train, individual pulses may have a duration of 20 milliseconds and given at a frequency of 50 Hz. Thus, in one particular embodiment, NGES may include high frequency electrical pulses of about 50 Hz, a train duration of about 6 seconds, a pulse duration of about 20 milliseconds, a pulse amplitude of about 10 volts and the electrical signal may be delivered in about 60 second intervals.

In a further embodiment of the present inventive method, an electrical signal generator device, as described in more detail herein, may be used to generate and deliver the electrical signals to the LES.

The present specification also provides for a device for electrical stimulation of the lower esophageal sphincter (LES) to modulate LES pressure. The device comprises one or more electrodes adapted for placement in contact with the LES tissue or in contact with a proximate region above or below the LES and an electrical signal generator to generate and deliver the electrical signal to the LES or a proximate region above or below the LES. In one embodiment, the electrical signal generator may be an implantable electrical signal generator. In another embodiment, the electrical signal generator may be a non-implanted device that delivers signals to the electrodes to stimulate the LES; for example, a device that is outside the body that may be worn by the subject.

In another embodiment, the present specification provides for a device for electrical stimulation of the esophagus in a region above the LES to lower esophageal pressure or treat esophageal spasms or nutcracker esophagus. The device comprises one or more electrodes adapted for placement in contact with esophageal tissue above the LES and an electrical signal generator to generate and deliver the electrical signal to the esophagus. In one embodiment, the electrical signal generator may be an implantable electrical signal generator. In another embodiment, the electrical signal generator may be a non-implanted device that delivers signals to the electrodes to stimulate the esophagus; for example, a device that is outside the body that may be worn by the subject.

The electrical signal generator may be any appropriate generator known in the art or any appropriate generator designed to generate and deliver the electrical signal to the LES, to a proximate region above or below the LES, or to the esophagus in a region above the LES. The electrical signal generator may be powered by any power source, method or system known in the art; for example, by a battery or by a power source outside the body that delivers energy to the electrical signal generator. In embodiments wherein the electrical signal generator is powered by battery, the battery may be replaceable and/or rechargeable by any method known in the art. The electrical signal generator may be programmed to generate and deliver an electrical signal comprising a variety of parameters. The parameters may include, but are not limited to frequency, train duration, pulse duration, pulse amplitude and interval.

Figure 7B:
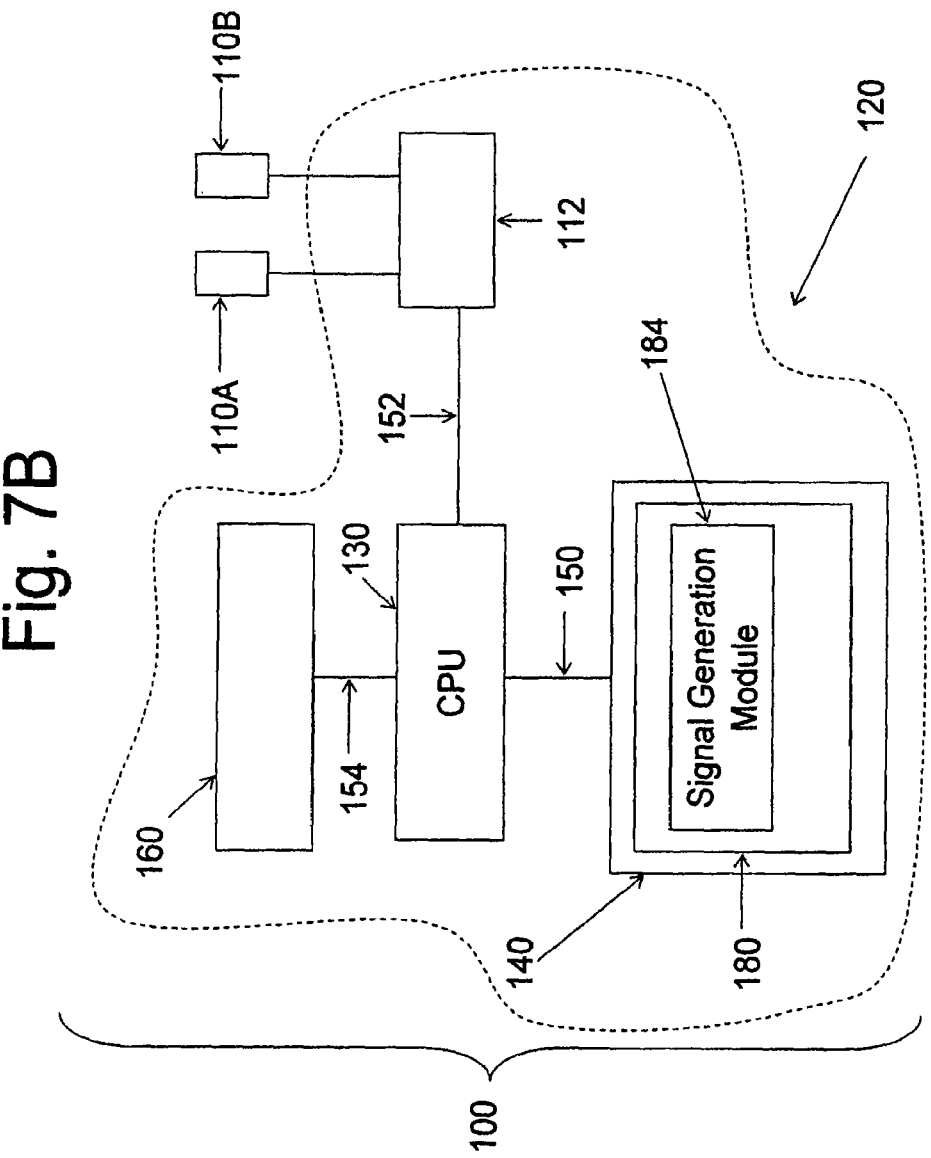
FIG. 7B depicts a block diagram illustrating various components of the electrical signal generator of FIG. 7A in accordance with one embodiment.

Referring to FIGS. 7A-7B, in one exemplary embodiment, the inventive electrical stimulation device 100 comprise one or more electrodes 110A and 110B adapted for placement in contact with the LES tissue, a proximate region above or below the LES, or a region of the esophagus above the LES to deliver electrical pulses thereto, and an electrical signal generator 120.

FIG. 7B is a block diagram of various components of the electrical stimulation device 100 of the present invention. The electrical stimulation device 100 may include a programmable central processing unit (CPU) 130, which may be implemented by any known technology, such as a microprocessor, microcontroller, application-specific integrated circuit (ASIC), digital signal processor (DSP), or the like. The CPU 130 may be integrated into an electrical circuit, such as a conventional circuit board, that supplies power to the CPU 130. The CPU 130 may include internal memory or memory 140 may be coupled thereto. The memory 140 is a computer readable medium that includes instructions or computer executable components that are executed by the CPU 130. The memory 140 may be coupled to the CPU 130 by an internal bus 150.

The memory 140 may comprise random access memory (RAM) and read-only memory (ROM). The memory 140 contains instructions and data that control the operation of the CPU 130. The memory 140 may also include a basic input/output system (BIOS), which contains the basic routines that help transfer information between elements within the electrical stimulation device 100. The present invention is not limited by the specific hardware component(s) used to implement the CPU 130 or memory 140 components of the electrical stimulation device 100.

The electrical stimulation device 100 may also include an external device interface 160 permitting the user or a medical professional to enter control commands, such as a command triggering the delivery of the electrical signals, commands providing new instructions to be executed by the CPU 130, commands changing parameters related to the electrical signal delivered by the electrical stimulation device 100, and the like, into the electrical stimulation device 100. The external device interface 160 may include a wireless user input device. The external device interface 160 may include an antenna (not shown) for receiving a command signal, such as a radio frequency (RF) signal, from a wireless user input device such as a computer-controlled programming wand. The electrical stimulation device 100 may also include software components for interpreting the command signal and executing control commands included in the command signal. These software components may be stored in the memory 140.

The electrical stimulation device 100 includes an electrical pulse interface 112 coupled to electrodes 110A and 110B for delivering the electrical pulses to the LES. The electrical pulse interface 112 may include any standard electrical interface known in the art for connecting a signal carrying wire to a conventional circuit board as well as any components capable of communicating a low voltage time varying signal generated by the CPU 130 or a signal generating device controlled by the CPU 130 to the electrodes 110A and 110B through an internal bus 152. The electrical pulse interface 112 may include hardware components such as memory as well as standard signal processing components such as a digital to analog converter, amplifiers, filters, and the like.

The various components of the electrical stimulation device 100 may be coupled together by the internal buses 150, 152, and 154. Each of the internal buses 150, 152, and 154 may be constructed using a data bus, control bus, power bus, I/O bus, and the like.

The electrical stimulation device 100 may include instructions 180 executable by the CPU 130 for generating an electrical signal delivered to the LES by the electrodes 110A and 110B. These instructions may include computer readable software components or modules stored in the memory 140.

The values of the various parameters may be stored in the memory 140 and used by the Signal Generation Module 184 to generate the electrical signal. The various parameters may be entered into the memory 140 by the external device interface 160 which permits the user or medical professional to enter control commands, including commands changing parameters related to the electrical signal delivered by the electrical stimulation device 100, and the like, into the electrical stimulation device 100.

While the electrical stimulation device 100 has been described as having the Signal Generation Module 184, embodiments in which the functionality of the Signal Generation Module 184 is performed by more than one software component are within the scope of the present invention.

The stimulation parameters (e.g., frequency, train duration, pulse duration, pulse amplitude, and intervals) may be individually optimized for each patient.

One method of variable programming of the electrical stimulation device 100 comprises a computer coupled to and used to program the computer-controlled programming wand. The programming wand may use radio frequency telemetry to communicate with the electrical stimulation device 100 and program the stimulation parameters of the electrical signal delivered by the electrical stimulation device 100 to the LES of the patient. Using the programming wand, programming may be performed periodically or as needed on the electrical stimulation device 100. This provides the ability to continually optimize and change the electrical signal delivered by the electrical stimulation device 100 depending on the LES pressure, and to respond to changes therein.

In one embodiment, the electrical stimulation device may be programmed to deliver low frequency electrical pulses to increase the LES pressure or to treat a condition or disease condition caused by or related to having abnormally low LES pressure. In a particular embodiment, the electrical stimulation device may be programmed to deliver a signal with frequencies of about 1 to about 60 pulses per minute. In another particular embodiment, the electrical stimulation device may be programmed to deliver a signal with frequencies of less than 20 pulses per minute. In another particular embodiment, the electrical stimulation device may be programmed to deliver a signal with frequencies of less than 15 pulses per minute. In another particular embodiment, the electrical stimulation device may be programmed to deliver a signal with frequencies of less than 10 pulses per minute. In another particular embodiment, the electrical stimulation device may be programmed to deliver a signal with a frequency of less than 5 pulses per minute. In another particular embodiment, the electrical stimulation device may be programmed to deliver a signal with a frequency of about 6 to about 7 pulses per minute. In another particular embodiment, the electrical stimulation device may be programmed to deliver a signal with a frequency of about 6 pulses per minute. The electrical stimulation device may also be programmed to deliver an electrical signal with a pulse duration of about 10 milliseconds to about 500 milliseconds. In a particular embodiment, the electrical stimulation device may be programmed to deliver an electrical signal with a pulse duration of 375 milliseconds. In yet another embodiment, the electrical stimulation device may be programmed to deliver an electrical signal with a pulse amplitude of about 5 mAmp to about 10 mAmp. In a particular embodiment, the electrical stimulation device may be programmed to deliver an electrical signal with a pulse amplitude of about 5 mAmp.

In another embodiment, wherein the object is to decrease the LES pressure, to treat a condition or disease condition caused by or related to having abnormally high LES pressure (e.g., achalasia), or to treat esophageal spasm or nutcracker esophagus, the electrical stimulation device may be programmed to deliver a signal with high frequency pulses. In particular embodiments, the high frequency pulses may be from about 5 Hz to about 100 Hz. In one particular embodiment, the high frequency pulses may be about 50 Hz. In another embodiment, the signal may comprise a train duration of about 2 milliseconds to about 300 microseconds. In a particular embodiment, the train duration may be about 50 microseconds to about 300 microseconds. In another particular embodiment, the train duration may be about 2 milliseconds to about 50 microseconds.

In another embodiment, the electrical stimulation device may be programmed to deliver neural gastric electric stimulation (NGES) to decrease the LES pressure, to treat a condition or disease condition caused by or related to having abnormally high LES pressure (e.g., achalasia), or to treat esophageal spasm or nutcracker esophagus. The NGES may have a frequency of about 5 Hz to about 100 Hz, a train duration of about 1 second to about 6 seconds, an amplitude of about 5 volts to about 10 volts, and a train interval of about 2 per minute to 1 every 5 minutes. In one particular embodiment, NGES may include a high frequency electrical pulses of about 50 Hz, a train duration of about 6 seconds, a pulse duration of about 20 milliseconds, a pulse amplitude of about 10 volts and the pulses may be delivered in about 60 second intervals.

The present invention also provides for a computer readable medium having computer executable instructions for applying any of the electrical signals described above. In one embodiment, the computer readable medium may have computer executable instructions for applying an electrical signal to stimulate the lower esophageal sphincter (LES) to modulate LES pressure in a subject in need thereof or to treat a condition or disease condition related to or caused by abnormal LES pressure in a subject in need thereof, comprising: instructions to generate and deliver an electrical signal comprising low frequency pulses to increase the LES pressure or to treat a condition or disease condition caused by or related to abnormally low LES pressure; or instructions to generate and deliver an electrical signal comprising high frequency pulses to decrease the LES pressure or to treat a condition or disease condition caused by or related to abnormally high LES pressure. The instructions to generate and deliver the electrical signal comprising low frequency pulses may further comprise instructions to generate and deliver a pulse duration of about 10 milliseconds to about 500 milliseconds and a pulse amplitude of about 5 mAmp to about 10 mAmp. In another embodiment, the instructions to generate and deliver the electrical signal comprising high frequency pulses may further comprise instructions to generate and deliver a train duration of about 2 millisecond to about 3000 microseconds. In another embodiment, the high frequency of the electrical signal may be a frequency of about 50 Hz and the instructions to generate and deliver the electrical signal comprising high frequency pulses may further comprise instructions to generate and deliver a train duration of about 6 seconds, a pulse duration of about 20 milliseconds, a pulse amplitude of about 10 volts and a pulse interval of about 60 seconds.

The methods of the invention can be readily effected by a range of devices and tools available in the art, and no more than routine experimentation is required to implement this invention in its various embodiments.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalents without the exercise of inventive capacity and without departing from the scope of the invention.

Example 1

The inventors conducted a study to determine if electrical stimulation of the lower esophageal sphincter can affect lower esophageal sphincter pressure and, if so, to explore the mechanisms by which electrical stimulation affects lower esophageal sphincter pressure.

Four female hound dogs (weight: 20-25 kg) underwent an esophagostomy that allowed the introduction of a sleeve manometry catheter into the esophagus; the sleeve was positioned at the lower esophageal sphincter. They were also implanted with a pair of electrodes along the longitudinal axis of the lower esophageal sphincter. The electrodes were exteriorized at the level of the neck.

After three weeks of recovery, the animals underwent esophageal manometry recording during control and electrical stimulation, performed randomly on separate days, using five different stimulations continuously recorded for one hour, as illustrated in the following table.

| Electrical Stimulation Type | Frequency | Train Duration (sec) | Pulse Duration (millisec) | Pulse Amplitude | Interval (sec) |
|---|---|---|---|---|---|
| Low Frequency | 6 cycles/min | — | 375 | 5 mAmp | Continuously |
| High Frequency | 50 Hz | 10 | 1 | 5 mAmp | 60 |
| High Frequency, circular | 20 Hz | 10 | 1 | 5 mAmp | 60 |
| NGES | 50 Hz | 6 | 20 | 10 Volts | 60 |
| Sham Stimulation | 0 | 0 | 0 | 0 | 0 |

All recordings were performed one hour after consumption of three ounces of canned dog food to prevent fluctuations in lower esophageal sphincter pressure, and under mild sedation (acepromazine 0.5 mg/kg). During electrical stimulation days, tests consisted of three periods of 20 minutes each: (1) control/baseline, (2) stimulation and (3) post-stimulation. Electrical stimulation was delivered using an external pulse generator. The effect of NGES was also tested under anesthesia and following administration of L-NAME 50 mg/kg IV and also atropine 0.05 mg/kg IV. Area under the curve ("AUC") and pressure were compared among the three periods. Data are shown as mean+/−SD, ANOVA and t-test, $p<0.05$.

Sustained increase in lower esophageal sphincter pressure was observed during low frequency stimulation: 32.1+/−12.8 vs. 42.4+/−18.0 vs. 50.1+/−23.6 (control vs. stimulation vs. post-stimulation, respectively; p=0.013; FIG. 1). AUC followed a similar pattern and significantly increased with low frequency electrical stimulation (3031.9+/−1428.6 vs. 1931.9+/−781.6, post-stimulation period compared to control; p<0.01; FIG. 1). There was no significant change with other types of electrical stimulation (FIGS. 2-5). Distinct changes in lower esophageal sphincter pressure were only observed during delivery of each NGES.

Example 2

Three female mongrel dogs underwent continuous recording of lower esophageal sphincter pressure under anesthesia. NGES was delivered to the lower esophageal sphincter for 10 minutes at: (1) baseline, (2) after L-NAME infusion (50 mg/kg) and (3) after atropine injection (0.05 mg/kg in the presence of L-NAME).

Changes in lower esophageal sphincter pressure during NGES are presented as percent change from preceding baseline. Results (FIG. 6) are presented as mean+/−SD.

|  | NGES | NGES + L-NAME | NGES + L-NAME + Atropine |
|---|---|---|---|
| Lower Esophageal Sphincter Pressure | 20.7 (3.7) | 35.7 (5.1)* | 24.1 (6.8) |
| Baseline (mmHg) Initial Peak (% change) | 31 (22.7) | 76 (48.6) | 27.3 (39.9) |
| Peak Duration (sec) | 1.5 (0.5) | 6.7 (3.9) | 3.9 (0.7) |
| Relaxation (% change) | 68.8 (28.6) | 28.2 (34.1)** | 20.4 (13.5)** |
| Relaxation Duration (sec) | 8.1 (0.8) | 4.4 (3.8) | 4.3 (3.8) |

*p < 0.001 when compared to NGES
**p < 0.05 when compared to NGES

Figure 6:
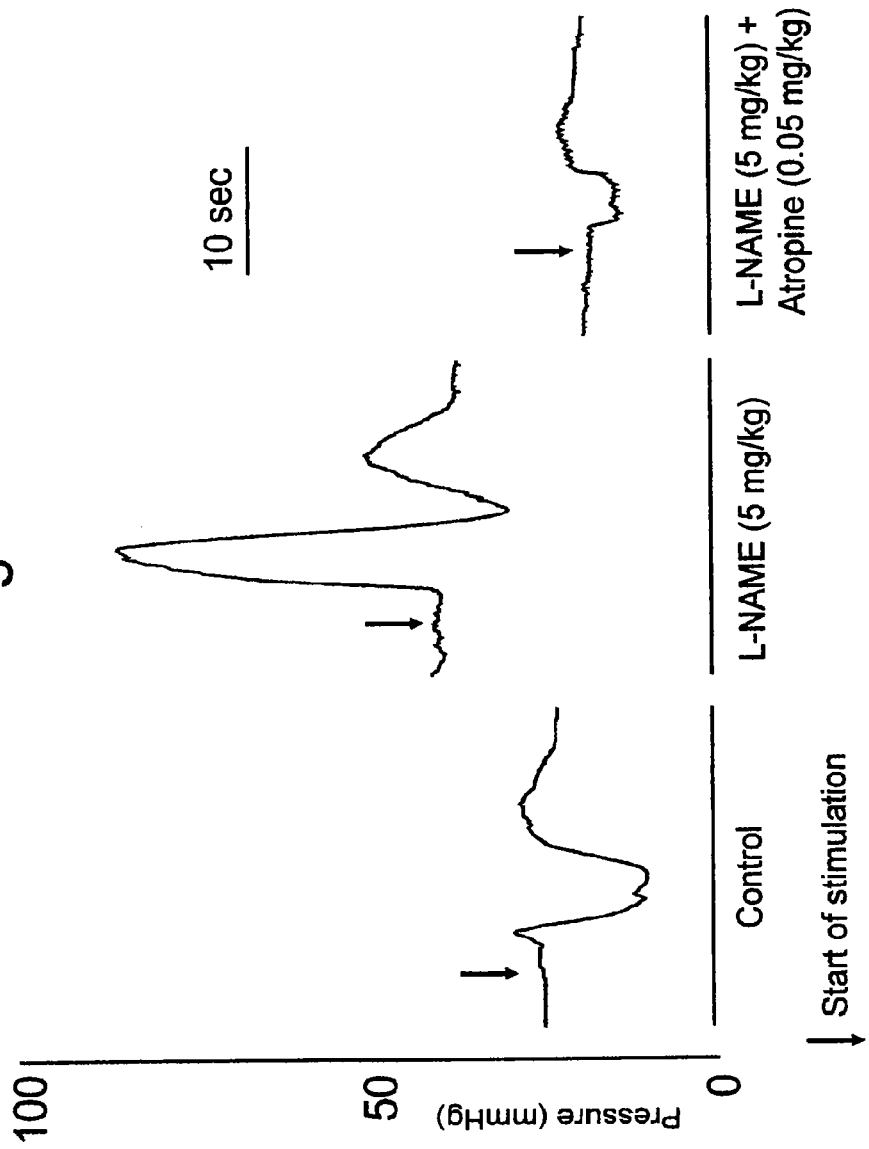
FIG. 6 depicts the effect of neural gastric electrical stimulation on lower esophageal sphincter pressure in accordance with one embodiment.

NGES induced an initial rise in lower esophageal sphincter pressure followed within a few seconds by relaxation with slow resumption of pressure over a one minute period (FIG. 6). L-NAME increased lower esophageal sphincter pressure and augmented the initial rise in lower esophageal sphincter pressure following NGES but markedly diminished or abolished the relaxation phase (FIG. 6). Atropine lowered lower esophageal sphincter pressure and abolished the initial rise in lower esophageal sphincter pressure induced by NGES (FIG. 6).

More particularly, NGES produces a biphasic response: an initial transient increase in lower esophageal sphincter pressure followed by lower esophageal sphincter relaxation, and subsequent return to baseline. L-NAME infusion increased baseline lower esophageal sphincter pressure, enhanced the initial increase in lower esophageal sphincter pressure and markedly suppressed lower esophageal sphincter relaxation. Subsequent addition of atropine reduced both baseline lower esophageal sphincter pressure and the NGES-induced rise in lower esophageal sphincter pressure.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

The invention claimed is:

1. A method of treating gastroesophageal reflux disease (GERD) in a subject in need thereof, comprising: providing an electrical signal; and delivering the electrical signal to a portion of a region encompassing a lower esophageal sphincter (LES) of said patient, wherein said region comprises the LES, 3 cm above the LES and 3 cm below the LES, to stimulate the LES and to increase the LES pressure, wherein said electrical signal is adapted to cause said LES pressure increase to be maintained for a period after stimulation ceases.

2. The method of treating GERD of claim 1 wherein said period is at least twenty minutes.

3. The method of treating GERD of claim 1, wherein delivering the electrical signal comprises using a stimulation device configured to generate and deliver the electrical signal to the portion of the region encompassing said LES.

4. The method of treating GERD of claim 3, wherein the stimulation device comprises: one or more electrodes adapted for placement in contact with the portion of the region encompassing said LES.

5. The method of treating GERD of claim 4, wherein at least a portion of the one or more electrodes is positioned on the LES.

6. The method of treating GERD of claim 4, wherein at least a portion of the one or more electrodes is positioned above the LES.

7. The method of treating GERD of claim 4, wherein at least a portion of the one or more electrodes is positioned below the LES.

8. The method of treating GERD of claim 4, wherein at least a portion of the one or more electrodes is positioned along a longitudinal axis of the LES.

9. The method of treating GERD of claim 1, wherein the electrical signal comprises low frequency electrical pulses to increase the LES pressure.

10. The method of treating GERD of claim 1, wherein the electrical signal comprises a pulse duration of about 10 milliseconds to about 500 milliseconds and a pulse amplitude of about 5 mAmp to about 10 mAmp.

11. A computer readable medium having computer executable instructions for applying an electrical signal to stimulate the lower esophageal sphincter (LES) to treat a condition or disease condition, comprising: instructions to generate and deliver an electrical signal, wherein said electrical signal is adapted to cause said LES pressure increase to be maintained for a period after stimulation ceases; and electrodes adapted to be implanted in a portion of a region encompassing the LES, wherein said region comprises the LES, 3 cm above the LES and 3 cm below the LES.

12. The computer readable medium of claim 11 wherein said period is at least twenty minutes.

13. The computer readable medium of claim 11, wherein the instructions to generate and deliver a pulse duration of about 10 milliseconds to about 500 milliseconds and a pulse amplitude of about 5 mAmp to about 10 mAmp.

14. The computer readable medium of claim 11, wherein delivering the electrical signal comprises using a stimulation device configured to generate and deliver the electrical signals to the portion of the region encompassing the LES.

15. The computer readable medium of claim 11, wherein at least a portion of the one or more electrodes is placed in contact with the LES.

16. The computer readable medium of claim 11, wherein at least a portion of the one or more electrodes is placed above the LES.

17. The computer readable medium of claim 11, wherein at least a portion of the one or more electrodes is placed below the LES.

18. The computer readable medium of claim 11, wherein the one or more electrode(s) are positioned along a longitudinal axis of the LES.

19. The computer readable medium of claim 11, wherein the condition or disease condition is selected from the group consisting of gastroesophageal reflux disease (GERD), food reflux, acid reflux, reflux esophagitis, chronic heart burn, gastroparesis, scleroderma, hypotensive lower esophageal sphincter, extraesophageal manifestations caused by reflux, achalasia, or combinations thereof.

20. The computer readable medium of claim 11, wherein the electrical signal comprises low frequency electrical pulses to increase the LES pressure.

* * * * *